United States Patent [19]

Hara et al.

[11] Patent Number: 4,861,931

[45] Date of Patent: Aug. 29, 1989

[54] PROCESS FOR PRODUCING 5-ALKYLIDENENORBORNENE

[75] Inventors: Yasuo Hara, Yokohama; Ryuji Oashi, Yokkaichi; Yoshitaka Kawahara, Ibaraki; Mikio Takeuchi, Yokkaichi, all of Japan

[73] Assignee: Japan Synthetic Rubber Co., Ltd., Tokyo, Japan

[21] Appl. No.: 208,667

[22] Filed: Jun. 20, 1988

[30] Foreign Application Priority Data

Jun. 23, 1987 [JP] Japan .............................. 62-156097

[51] Int. Cl.$^4$ ............................................. C07C 5/25
[52] U.S. Cl. ..................................................... 585/363
[58] Field of Search .......................................... 585/363

[56] References Cited

U.S. PATENT DOCUMENTS

| | | | |
|---|---|---|---|
| 3,897,510 | 7/1975 | Kiyoto | 585/363 |
| 3,957,895 | 5/1976 | Matsuno | 585/363 |
| 4,205,192 | 5/1980 | Harada | 585/363 |

FOREIGN PATENT DOCUMENTS

| | | | |
|---|---|---|---|
| 0591447 | 7/1972 | U.S.S.R. | 585/363 |
| 1362855 | 8/1974 | United Kingdom . | |

OTHER PUBLICATIONS

English Abstract of Japanese Patent 35,264/74.
English Abstract of Japanese Patent 43,055/82.
English Abstract of United Kingdom Patent 1,148,153.
English Abstract of Japanese Patent 24,138/70.
English Abstract of Japanese Patent 35,072/75.

*Primary Examiner*—Curtis R. Davis
*Attorney, Agent, or Firm*—Oblon, Spivak, McClelland, Maier & Neustadt

[57] ABSTRACT

A process for producing a 5-alkylidene-norbornene, which comprises contacting a 5-alkenyl-norbornene with an organolithium compound and at least one compound selected from the group consisting of ammonia, a hydrazine compound and an aliphatic amine compound wherein at least one nitrogen atom in the molecule bonds to at least one hydrogen atom to isomerize the 5-alkenylnorbornene. This process enables the easy and efficient production of a 5-alkylidenenorbornene from an easily available raw material.

16 Claims, No Drawings

PROCESS FOR PRODUCING 5-ALKYLIDENENORBORNENE

This invention relates to a process for producing a 5-alkylidenenorbornene easily and efficiently by isomerizing a 5-alkenylnorbornene which is a relatively easily commercially available raw material. 5-Alkylidenenorbornenes are used as, for example, a third component in ethylene-propylene copolymer rubber and are very important in industry.

5-Ethylidenenorbornene (hereinafter abbreviated to ENB), a typical 5-alkylidenenorbornene, can be directly produced from 1,2-butadiene and cyclopentadiene by subjecting them to a Diels-Alder reaction (see Japanese Patent Publication No. 39,255/74). This process is the simplest in view of the reaction technique for 5-ethylidenenorbornene production but it is difficult to secure the starting 1,2-butadiene. Hence, in the commercial production of 5-ethylidenenorbornene, generally, 1,3-butadiene and cyclopentadiene are first converted to 5-vinylnorbornene (hereinafter abbreviated to VNB) by Diels-Alder reaction and this VNB is then converted to ENB by isomerization.

There are various proposals for the isomerization of VNB. In these proposals, generally, VNB is contacted with, for example, an acidic reagent, an alkali metal, a mixture of a basic reagent with a polar organic solvent or the like to isomerize VNB to ENB. When an acidic reagent is used, however, the starting diolefin polymerizes and hence it is impossible to obtain ENB in a high yield. When an alkali metal is used, generally there are used (1) a method comprising contacting VNB with an alkali metal supported on a carrier (see Japanese Pat. Publication Nos. 35,264/74 and 43,055/82 and the like) and (2) a method comprising contacting VNB with a solution of an alkali metal in a polar organic solvent (see U.K. Pat. No. 1,148,153 and the like). In these methods, however, an alkali metal such as metallic potassium, metallic sodium, metallic lithium or the like is used, and hence handling is very difficult.

As the method wherein a basic reagent-polar organic solvent mixture is used, the following methods are proposed: (1) a method comprising contacting VNB with an alkali metal amide-nitrogen base mixture (see Japanese Pat. Publication No. 24,138/70) and (2) a method comprising contacting VNB with an alkali metal hydride-dimethyl sulfoxide mixture (see U.S. Pat. No. 3,591,647) or with an alkali metal hydride-aliphatic amine mixture (see Japanese Patent Publication No. 35,072/75). In these methods, however, the alkali metal amide (e.g. sodium amide or the like) is too expensive to use it commercially, and the alkali metal hydride generates heat and hydrogen when it reacts with dimethyl sulfoxide or an aliphatic amine and in addition requires a large amount of a polar organic solvent, and hence, a reactor of large capacity.

Besides the above-mentioned methods, a method is proposed wherein a potassium tertiary butoxide-dimethyl sulfoxide mixture is used (see Japanese Patent Publication No. 24,138/70). In this method, however, since the isomerization activity of the mixture is not so high, large amounts of potassium tertiary butoxide and dimethyl sulfoxide are required in order to obtain a high conversion of VNB and ENB, and a long time is required for the reaction. Moreover, the potassium tertiary butoxide used in the above reaction system is very expensive and is difficult to obtain commercially.

The present inventors have made extensive research to solve the above-mentioned problems in the prior art and found that a 5-alkylidenenorbornene can be produced efficiently by isomerizing a 5-alkenylnorbornene in the presence of an organolithium compound and at least one compound selected from the group consisting of ammonia, a hydrazine compound and an aliphatic amine compound wherein at least one nitrogen atom in the molecule bonds to at least one hydrogen atom.

According to this invention, there is provided a process for producing a 5-alkylidenenorbornene, which comprises contacting a 5-alkenylnorbornene with an organolithium compound and at least one compound selected from the group consisting of ammonia, a hydrazine compound and an aliphatic amine compound wherein at least one nitrogen atom in the molecule bonds to at least one hydrogen atom, to isomerize the 5-alkenylnorbornene.

The organolithium compound used in this invention includes methyllithium, ethyllithium, butyllithium, amyllithium, hexyllithium, 2-ethylhexyllithium, phenyllithium, tolyllithium, xylyllithium, α-naphthyllithium, methylenedilithium, tetramethylenedilithium, 1,4-dilithiumbenzene, 1,5-dilithiumnaphthalene, etc.

In this invention, these organolithium compounds can be used alone or in combination of two or more.

The organolithium compound is used in an amount of preferably 0.1 to 100 millimoles, more preferably 0.5-50 millimoles per mole of the 5-alkenylnorbornene. When the amount is too small, the rate of isomerization is low. When the amount is too large, not only is the process economically disadvantageous, but also side reactions (e.g. polymerization) are promoted and the efficient production of the desired alkylidenenorbornene becomes difficult.

The aliphatic amine compound used in this invention, in which at least one nitrogen atom in the molecule bonds to at least one hydrogen atom, includes saturated aliphatic primary amines such as methylamine, ethylamine, n-propylamine, isopropylamine, n-butylamine, isobutylamine, n-hexylamine, laurylamine and the like; saturated aliphatic secondary amines such as dimethylamine, diethylamine, dibutylamine and the like; saturated aliphatic diamines such as ethylenediamine, tetramethylenediamine, hexamethylenediamine and the like; monoalkyldiamines, dialkyldiamines and trialkyldiamines obtained by substituting an alkyl group or alkyl groups for a part of the hydrogen atoms of the saturated aliphatic diamines bonding to the nitrogen atoms such as monoalkyldiamines (e.g., N-methylethylenediamine, N-ethylethylenediamine, N-methyltetramethylenediamine, N-ethyltetramethylenediamine, N-methylhexamethylenediamine, N-ethylhexamethylenediamine and the like), dialkyldiamines (e.g., N,N'-dimethylethylenediamine, N,N'-diethylethylenediamine, N,N'-dimethyltetramethylenediamine, N,N'-diethyltetramethylenediamine, N,N'-dimethylhexamethylenediamine, N,N'-diethylhexamethylenediamine, N,N-dimethylethylenediamine, N,N-diethylethylenediamine, N,N-dimethyltetramethylenediamine, N,N-diethyltetramethylenediamine, N,N-dimethylhexamethylenediamine, N,N-diethylhexamethylenediamine and the like) and trialkyldiamines (e.g., N,N,N'-trimethylethylenediamine, N,N,N'-triethylethylenediamine, N,N,N'-trimethyltetramethylenediamine, N,N,N'-triethyltetramethylenediamine, N,N,N'-trimethylhexamethylenediamine, N,N,N'-triethylhexamethylenediamine and the like); saturated aliphatic polyamines such as diethylenetriamine, triethyltetramine and the like; alkylpolyamines obtained by substituting an alkyl group or alkyl groups for a part of the hydrogen atoms of the saturated aliphatic polyamines bonding to the nitrogen atoms such as N-methyldiethylenetriamine, N'-methyldiethylenetriamine, N,N''-dimethyldiethylenetriamine, N,N',N''-trimethyldiethylenetriamine, N-methyltriethylenetetramine, N,N'''-dimethyltriethylenetriamine, N',N''-dimethyltriethylenetriamine and the like; and alicyclic amines such as piperidine, pyrrolidine and the like, and compounds similar thereto. In the aliphatic amine compounds, the proportion of the number of the N-H bonds to the total number of the N-C bonds and the N-H bonds is preferably at least 15%, more preferably at least 30%, particularly preferably at least 50% and most preferably at least 60%. Also, it is preferable that each nitrogen atom in the molecule has at least one hydrogen atom. These amine compounds can be used alone or in combination of two or more.

The hydrazine compound includes hydrazine, monoalkylhydrazines, dialkylhydrazines and trialkylhydrazines. These hydrazine compounds can be used alone or in combination of two or more.

The compounds selected from the group consisting of ammonia, a hydrazine compound and an aliphatic amine compound can be used alone or in combination of two or more.

The above-mentioned at least one compound selected from the group consisting of ammonia, a hydrazine compound and aliphatic amines is used in an amount of preferably 1–1,000 moles, more preferably 10–100 moles, per mole of the organolithium compound. When the amount is less than 1 mole, the isomerization rate of 5-alkenylnorbornene to 5-alkylidenenorbornene is low. When the amount is more than 1,000 moles, the process becomes disadvantageous economically, and in some cases, the water contained in a very small amount in the aliphatic amines, the ammonia and the hydrazine compounds results in decomposition of the organolithium compound and it follows that the isomerization reaction does not proceed.

Typical examples of the 5-alkenylnorbornene used in the present process as the starting material and the 5-alkylidenenorbornene produced by the present process are as follows:

| 5-Alkenylnorbornene | | 5-Alkylidenenorbornene |
|---|---|---|
| 5-Vinylnorbornene | → | 5-Ethylidenenorbornene |
| 5-Propenylnorbornene | → | 5-Propylidenenorbornene |
| 5-Butenylnorbornene | → | 5-Butylidenenorbornene |
| 5-Decenylnorbornene | → | 5-Decenylidenenorbornene |

As a matter of course, the 5-alkenylnorbornene and 5-alkylidenenorbornene in the present process are not restricted to the above specific compounds.

In carrying out the present process, a 5-alkenylnorbornene can be easily isomerized by adding the 5-alkenylnorbonene to an organolithium compound and at least one compound selected from the group consisting of ammonia, a hydrazine compound and an aliphatic amine compound wherein at least one nitrogen atom in the molecule bonds to at least one hydrogen atom. The addition order of these reactants is not critical.

In carrying out the present process, the reaction temperature is not critical, though it is preferably 10°–250° C., more preferably 50°–180° C. When the reaction temperature is too low, the isomerization rate of 5-alkenylnorbornene to 5-alkylidenenorbornene is low and the reaction efficiency becomes low. When the reaction temperature is too high, side reactions such as polymerization and the like proceed more, whereby the yield and selectivity of the desired 5-alkylidenenorbornene become lower.

In carrying out the present process, a solvent may be used if necessary. Such a solvent must not react with any of the 5-alkenylnorbornene, the 5-alkylidenenorbornene, the organolithium compound, the aliphatic amine compound, the ammonia and the hydrazine compound, and is preferably a saturated hydrocarbon having 5–10 carbon atoms.

In the present process, the reaction manner is not critical and may be continuous or batchwise.

According to the process of this invention, a 5-alkylidenenorbornene can be easily and efficiently produced by isomerizing a 5-alkenylnorbornene which is a raw material relatively easy to obtain commercially. In this process, the organolithium compound, the aliphatic amine compound, the ammonia, the hydrazine compound, etc. separated from the isomerization system by a means such as distillation or the like can be used again in fresh isomerization reaction, whereby the production cost of the 5-alkylidenenorbornene can be reduced.

This invention is explained in more detail below referring to Examples. However, this invention should not be construed to be restricted to the Examples.

The yield and selectivity of 5-alkylidenenorbornene mentioned in the Examples and Comparative Examples were calculated from the following equations using the results of gas chromatography:

Yield (%)=(Amount of 5-alkylidenenorbornene obtained)÷(amount of alkenylnorbornene fed)×100

Selectivity (%)=(Amount of 5-alkylidenenorbornene obtained)÷(amount of 5-alkenylnorbornene isomerized)×100

Conditions of gas chromatography

Capillary column: DEGS 70 m (number of theoretical plates=100,000)
Column temperature: 70° C.
Injection temperature: 200° C.
Detector: FID
Internal standard: n-Tridecane

EXAMPLES 1–10 AND COMPARATIVE EXAMPLES 1–3

A 100-ml, three-necked flask provided with a refluxing tube and a thermometer was used as a reactor. Into this reactor were charged 30 g of a 5-alkenylnorbornene, a predetermined amount of an organolithium compound and a predetermined amount of an aliphatic amine compound (these are specifically shown in Table 1) in a nitrogen stream. The mixture was stirred with a magnetic stirrer for 3 hours while being kept at a predetermined temperature as shown in Table 1 to conduct isomerization reaction.

The results are shown in Table 1.

EXAMPLE 11

In a 100-ml stainless steel autoclave were placed 50 g of 5-vinylnorbornene, 0.13 g of n-butyllithium and 1.1 g of ammonia in a nitrogen atmosphere. The mixture was subjected to isomerization reaction at 100° C. for 3 hours with stirring.

As a result, 5-ethylidenenorbornene was obtained in a yield of 88.0% and at a selectivity of 100%.

EXAMPLE 12

The same procedure as in Example 11 was repeated, except that 2.0 g of hydrazine was used in place of the ammonia.

As a result, 5-ethylidenenorbornene was obtained in a yield of 89.3% and at a selectivity of 100%.

TABLE 1

| | 5-Alkenyl-norbornene (a) | Organolithium compound (b) | Aliphatic amine compound (c) |
|---|---|---|---|
| Example 1 | 5-Vinylnorbornene | n-Butyllithium | Ethylenediamine |
| 2 | " | " | " |
| 3 | " | " | " |
| 4 | " | " | " |
| 5 | " | " | Diethylenetriamine |
| 6 | " | " | " |
| 7 | " | " | Dibutylamine |
| 8 | " | Isobutyllithium | Ethylenediamine |
| 9 | " | t-Butyllithium | " |
| 10 | 5-Propenylnorbornene | n-Butyllithium | " |
| Comparative Example 1 | 5-Vinylnorbornene | n-Butyllithium | Tetramethylethylenediamine |
| 2 | " | " | — |
| 3 | " | — | Ethylenediamine |

| (b)/(a)*1 | (c)/(b)*2 | Reaction temperature (°C.) | Yield (%) | Selectivity (%) |
|---|---|---|---|---|
| 5 | 30 | 80 | 98.7 | 100 |
| 0.5 | 50 | 110 | 80.1 | 100 |
| 30 | 30 | 50 | 87.3 | 100 |
| 10 | 10 | 80 | 91.4 | 100 |
| 3 | 30 | 100 | 97.4 | 100 |
| 1 | 50 | 130 | 85.5 | 100 |
| 30 | 80 | 60 | 77.7 | 100 |
| 5 | 30 | 60 | 88.2 | 100 |
| 5 | 30 | 60 | 89.4 | 100 |
| 5 | 30 | 80 | 97.8 | 100 |
| 50 | 50 | 110 | 22.7 | 100 |
| 100 | — | 110 | 2.1 | 100 |
| — | *3 | 110 | 0 | — |

Note:
*1Millimoles of (b) per mole of (a)
*2Molar ratio
*3Ethylenediamine was used in a proportion of 2.5 moles per mole of 5-vinyl-norbornene.

What is claimed is:

1. A process for producing a 5-alkylidenenorbornene, which comprises contacting a 5-alkenylnorbornene with an organolithium compound and at least one compound selected from the group consisting of ammonia, a hydrazine compound and an aliphatic amine compound wherein at least one nitrogen atom in the molecule bonds to at least one hydrogen atom, to isomerize the 5-alkenylnorbornene.

2. The process according to claim 1, wherein the organolithium compound is used in an amount of 0.1–100 millimoles per mole of the 5-alkenylnorbornene and the amount of the above at least one compound used is 1–1,000 moles per mole of the organolithium compound.

3. The process according to claim 2, wherein the amount of the organolithium compound used is 0.5–50 millimoles per mole of the 5-alkenylnorbornene.

4. The process according to claim 1, wherein the organolithium compound is at least one compound selected from the group consisting of methyllithium, ethyllithium, butyllithium, amyllithium, hexyllithium, 2-ethylhexyllithium, phenyllithium, tolyllithium, xylyllithium, α-naphthyllithium, methylenedilithium, tetramethylenedilithium, 1,4-dilithiumbenzene and 1,5-dilithiumnaphthalene.

5. The process according to claim 1, wherein the aliphatic amine compound is at least one compound selected from the group consisting of saturated aliphatic primary amines, saturated aliphatic secondary amines, saturated aliphatic diamines, monoalkyl-substituted saturated aliphatic diamines, dialkyl-substituted saturated aliphatic diamines, trialkyl-substituted saturated aliphatic diamines, saturated aliphatic polyamines, alkyl-substituted saturated aliphatic polyamines and alicyclic amines.

6. The process according to claim 5, wherein the saturated aliphatic primary amines include methylamine, ethylamine, n-propylamine, isopropylamine, n-butylamine, isobutylamine, n-hexylamine and laurylamine; the saturated aliphatic secondary amines include dimethylamine, diethylamine and dibutylamine; the saturated aliphatic diamines include ethylenediamine, tetramethylenediamine and hexamethylenediamine; the monoalkyl-substituted saturated aliphatic diamines include monoalkyl-substituted ethylenediamines, monoalkyl-substituted tetramethylenediamines, and monoalkyl-substituted hexamethylenediamines; the dialkyl-substituted saturated aliphatic diamines include dialkyl-substituted ethylenediamines, dialkyl-substituted tetramethylenediamines and dialkyl-substituted hexamethylenediamines; the trialkyl-substituted saturated aliphatic diamines include trialkyl-substituted ethylenediamines, trialkyl-substituted tetramethylenediamines and trialkyl-substituted hexamethylenediamines; the saturated aliphatic polyamines include diethylenetriamine and triethyltetramine; the alkyl-substituted saturated aliphatic polyamines include alkyl-substituted diethylenetriamines and alkyl-substituted triethyltetramines; and the alicyclic amines include piperidine and pyrrolidine.

7. The process according to claim 1, wherein the hydrazine compound is at least one compound selected from the group consisting of hydrazine, monoalkylhydrazines, dialkylhydrazines and trialkylhydrazines.

8. The process according to claim 1, wherein the amount of the above at least one compound used is 10–100 moles per mole of the organolithium compound.

9. The process according to claim 1, wherein the 5-alkenylnorbornene has an alkyl group of 2–10 carbon atoms.

10. The process according to claim 1, wherein the 5-alkenylnorbornene is at least one compound selected from the group consisting of 5-vinylnorbornene, 5-propenylnorbornene, 5-butenylnorbornene and 5-decenylnorbornene.

11. The process according to claim 1, wherein the 5-alkenylnorbornene is 5-vinylnorbornene.

12. The process according to claim 1, wherein the 5-alkylidenenorbornene has an alkylidene group of 2–10 carbon atoms.

13. The process according to claim 1, wherein the 5-alkylidenenorbornene is at least one compound selected from the group consisting of 5-ethylidenenorbornene, 5-propylidenenorbornene, 5-butylidenenorbornene and 5-decenylidenenorbornene.

14. The process according to claim 1, wherein the 5-alkylidenenorbornene is 5-ethylidenenorbornene.

15. The process according to claim 1, wherein the isomerization reaction is conducted at a temperature between 10° C. and 250° C.

16. The process according to claim 1, wherein the isomerization reaction is conducted at a temperature between 50° C. and 180° C.

* * * * *